US008719945B2

(12) United States Patent
Birtwhistle et al.

(10) Patent No.: US 8,719,945 B2
(45) Date of Patent: May 6, 2014

(54) CUSTOMER ERROR SCREEN CAPTURE

(75) Inventors: Daniel P. Birtwhistle, Fishers, IN (US); Robert E. Reinke, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 68 days.

(21) Appl. No.: 13/400,396

(22) Filed: Feb. 20, 2012

(65) Prior Publication Data
US 2013/0167245 A1 Jun. 27, 2013

Related U.S. Application Data

(60) Provisional application No. 61/579,190, filed on Dec. 22, 2011.

(51) Int. Cl.
*G06F 21/00* (2013.01)
(52) U.S. Cl.
USPC .............. 726/26; 726/27; 380/243; 380/244; 380/245; 380/246
(58) Field of Classification Search
USPC ..................................... 726/26–27
See application file for complete search history.

(56) References Cited

U.S. PATENT DOCUMENTS

| 2004/0139156 | A1 | 7/2004 | Matthews et al. |
| 2007/0061266 | A1 | 3/2007 | Moore et al. |
| 2007/0095354 | A1 | 5/2007 | Churchill et al. |
| 2008/0256399 | A1* | 10/2008 | Erdosi et al. .................... 714/47 |
| 2009/0150825 | A1 | 6/2009 | Yokoyama et al. |
| 2009/0164878 | A1 | 6/2009 | Cottrille |
| 2009/0217163 | A1* | 8/2009 | Jaroker ........................ 715/700 |
| 2010/0131551 | A1 | 5/2010 | Benzaken et al. |
| 2010/0241844 | A1 | 9/2010 | Hussain et al. |
| 2011/0202798 | A1 | 8/2011 | Vera et al. |
| 2012/0046972 | A1 | 2/2012 | Tonti et al. |
| 2012/0066757 | A1 | 3/2012 | Vysogorets et al. |
| 2012/0089860 | A1 | 4/2012 | Zaifman et al. |

FOREIGN PATENT DOCUMENTS

| EP | 2375353 | 10/2011 |
| WO | WO2006104810 | 10/2006 |

OTHER PUBLICATIONS

45 Code of Federal Regulations, 164.52B—Accounting of Disclosures of Protected Health Information; revised as of Oct. 1, 2010.

* cited by examiner

*Primary Examiner* — Ghazal Shehni
(74) *Attorney, Agent, or Firm* — Harness, Dickey

(57) ABSTRACT

A method for capturing a user's view of an electronic screen having an error message in a health management application without showing private information of the user includes receiving an error message from a web service responding to a request for a web page by the user. The method includes receiving an electronic file of the web page with the error message, redacting private information of the user from the electronic file to create a redacted electronic file, and storing the redacted electronic file in a support log module.

19 Claims, 4 Drawing Sheets

CUSTOMER ERROR SCREEN CAPTURE

CROSS-REFERENCE TO RELATED APPLICATIONS

This application claims the benefit of U.S. Provisional Application No. 61/579,190, filed on Dec. 22, 2011. The entire disclosure of the above application is incorporated herein by reference.

FIELD

The present disclosure relates to a system for providing customer support by accessing a user's web browser session that has been redacted to restrict access to private data of the user.

BACKGROUND

Title II of the Health Insurance Portability and Accountability Act (HIPAA) includes a Privacy Rule. The HIPAA Privacy Rule regulates the use and disclosure of certain information held by "covered entities" including health insurers, medical service providers and others that engage in certain transactions. The Privacy Rule establishes regulations for the use and disclosure of Protected Health Information (PHI) regarding health status, provision of health care, or payment for health care associated with an individual or patient. PHI covers, among other information, any part of an individual's medical record or payment history. A covered entity may disclose PHI to facilitate treatment, payment, or health care operation or if the covered entity has obtained authorization from the individual.

Additionally, when a covered entity discloses any PHI, it must make a reasonable effort to disclose only the minimum necessary information required to achieve its purpose. Increasingly, many patients, especially patients with chronic conditions that require daily management, such as diabetes, participate in health care management plans that include using software to manage, monitor, log, update and transfer data to a health management service or a participating health provider. Typically, a user (patient or health professional) interacts with software provided by the health management service or other health professional. The software can be in the form of an application or program which resides in a computer device (PC, laptop, tablet, smartphone or other handheld device) of the user or communicates with a web service of a health management service or provider by means of a web browser of the user. When an error occurs during the use of the application, the user can communicate by telephone or e-mail, or other digital communication with a support service. The support person that receives the call may not, however, be able to reproduce the error to determine the cause of the problem without seeing what the user sees and without tracing the user's actions. Permission to see private information of the user must be sought and saved in an audit log according to the PHI rule of HIPAA. Even when such permission is received, the experience may not be comfortable for the user and support member.

In the exemplary case of patients with diabetes, for example, diabetes is managed primarily by controlling the level of glucose in the bloodstream (bG). This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Generally, management of diabetes is time-consuming for patients because of the need to consistently obtain reliable diagnostic information, follow prescribed therapy, and manage lifestyle on a daily basis. Diagnostic information, such blood glucose, is typically obtained from a capillary blood sample with a lancing device and is then measured with a handheld blood glucose meter. Interstitial glucose levels can be obtained from a continuous glucose sensor worn on the body. Prescribed therapies can include insulin, oral medications, or both. Insulin can be delivered with a syringe, an ambulatory infusion pump, an insulin patch or combinations thereof. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data acquired in a variety of ways: from medical devices, from personal healthcare devices, from patient recorded logs, from laboratory tests, and from healthcare professional recommendations. Medical devices include bG meters, continuous glucose monitors, ambulatory insulin infusion pumps, diabetes analysis software, and diabetes device configuration software. Each of these systems generates and/or manages large amounts of diagnostic and prescriptive data. Personal healthcare devices include weight scales, and blood pressure cuffs, exercise machines, thermometers, and weight management software. Patient recorded logs include information relating to meals, exercise and lifestyle. Lab test results include HbA1C, cholesterol, triglycerides, and glucose tolerance. Recommendations by healthcare professionals may include prescriptions, diets, test plans, and other information relating to the patient's treatment.

At the interaction of a patient or health professional with software used by the patient and health professional in the management of diabetes as describe above, software or other application errors can be encountered in association with files, forms or screen views that also include personal, medical and other health information of the patient that is protected by the Privacy Rule of HIPAA (private information).

The present teachings are directed to addressing this problem by accessing a user's web browser session that has been redacted to restrict access to private data of the user, including personal, medical or other protected information of the user.

SUMMARY

This section provides a general summary of the disclosure, and is not a comprehensive disclosure of its full scope or all of its features.

The present teachings provide a method for capturing a user's view of an electronic screen having an error message in a health management application without showing private information of the user. The method includes receiving an error message from a web service responding to a request for a web page by the user, receiving an electronic file of the web page with the error message, redacting private information of the user from the electronic file to create a redacted electronic file and storing the redacted electronic file in a support log module.

In some embodiments, the method includes receiving an error message from a web service responding to a request for a web page by the user and receiving an electronic file of the web page with the error message to a logging service communicating with the web service. The method also includes identifying fields pre-tagged as private information in the electronic file and redacting values associated with the pre-tagged fields to create a redacted electronic file, rendering the redacted electronic file to an image file, and storing the image file in a support log module.

The present teachings also include a system for capturing a user's view of an electronic screen having an error message associated with a health management application without showing private information of the user. The system includes a logging service programmed to receive an electronic file with an error message from a user's electronic screen and transfer the electronic file for sanitization. The system includes a sanitization module programmed to receive the electronic file with the error message, redact private information of the user and create a redacted electronic file. The system includes a support log for receiving and storing the redacted electronic file, and a support application communicating with the support log and programmed to retrieve the redacted electronic file for delivery to a support person's processing device.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
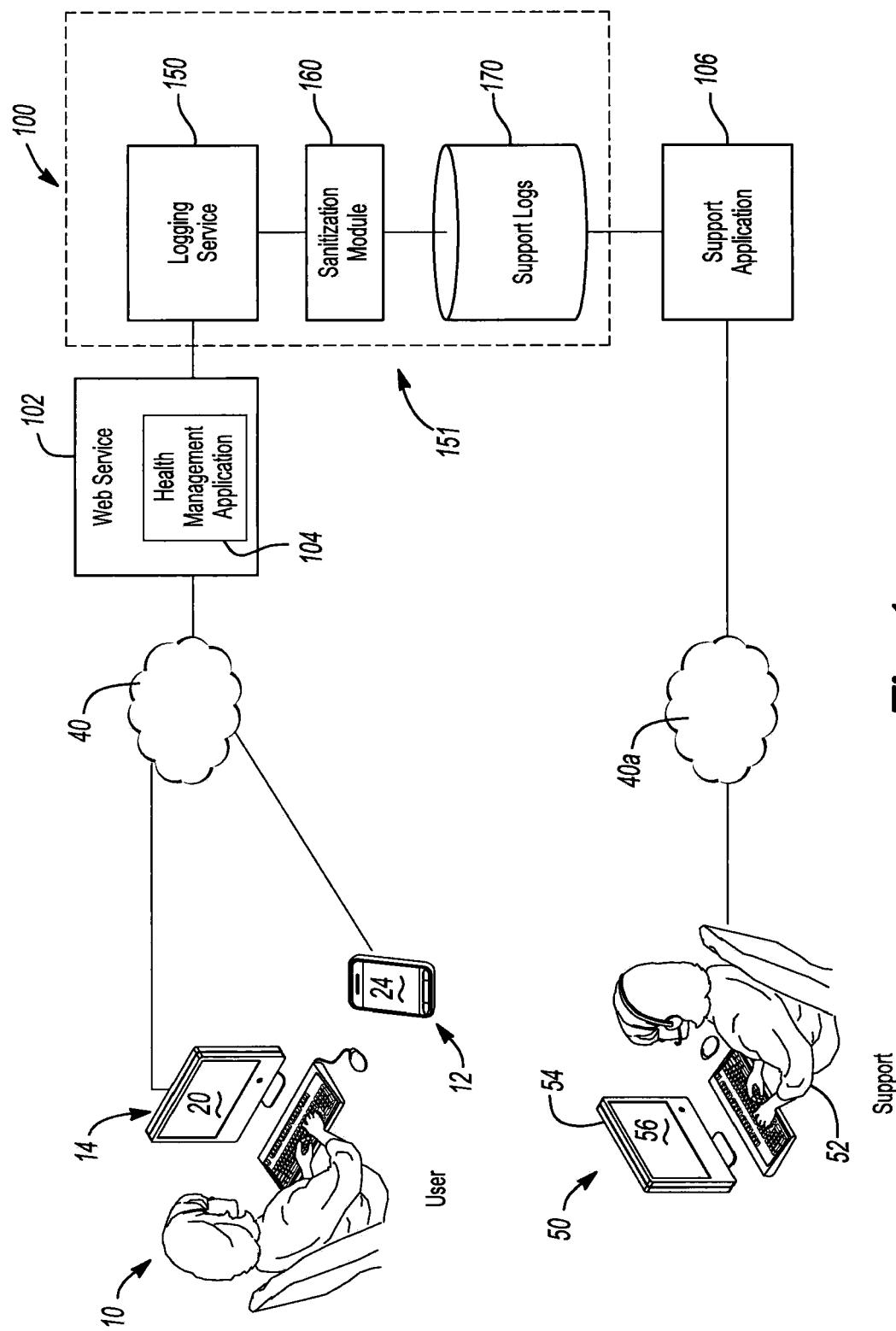
FIG. 1 illustrates an exemplary diagram of a system according to the present teachings.

The following description is merely illustrative in nature and is in no way intended to limit the disclosure, its application, or uses. For purposes of clarity, the same reference numbers will be used in the drawings to identify similar elements.

FIG. 1 shows a diagram for a system 100 for capturing a user's electronic screen having an error message and providing a redacted version to a customer support service after removing sensitive or protected personal and medical data of the user (private information), according to the present teachings. For clarity, the system 100 is described in the context of health management, such as diabetes, but the present teachings are applicable to any other systems in which a user needs customer support for a computer-implemented application from a provider of the service for the application without having to share certain private information or other confidential information.

Figure 3:
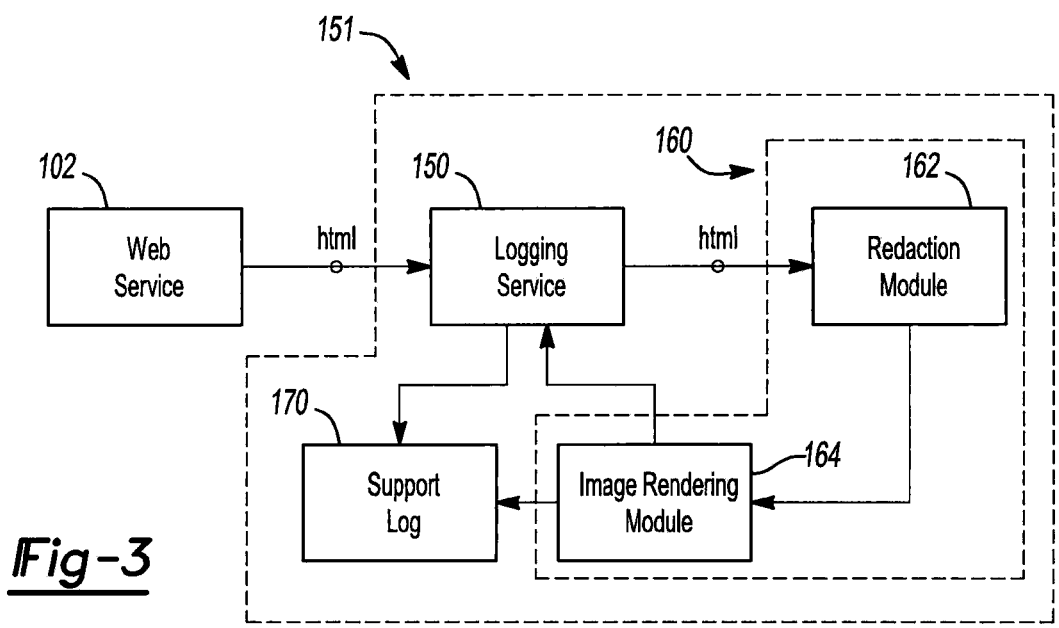
FIG. 3 is an exemplary block diagram of a system according to the present teachings.

Briefly, and referring to FIGS. 1 and 3, the system 100 includes a web service 102 associated with a health management application (software program or module) 104, a logging service (or logging module) 150, a sanitization module (software) 160, a support log or support database 170 and a support application (software) 106. The sanitization module 160 can include a redaction module 162 and an image rendering module 164. The logging service 150 and the sanitization module 160 can be included in a logging application 151. The logging application 151 may optionally include the support log 170 and/or the support application 106. A user 10 can communicate with the web service 102 and/or the health management module 104 via a communication network 40. A support person 52 at a customer support service 50 can communicate with the support application 106 via a communications network 40a. The support person 52 can also communicate with the web service 102 and/or health management application 104 directly or indirectly, although direct link is not shown in FIG. 1. The communication networks 40 and 40a can be public or private networks and can be separate and/or linked.

The user 10 can be either a patient, such as a person with diabetes, or a health care provider that can interact with the web service 102 to access an application, such as the health management application 104. Generally, persons with diabetes include persons with metabolic syndrome, pre-diabetes, type 1 diabetes, type 2 diabetes, gestational diabetes, and other types of diabetes and are collectively referred to as the patient herein. Healthcare providers for diabetes are diverse and include nurses, nurse practitioners, physicians, and endocrinologists and are collectively referred to as the clinician herein. Accordingly, the user 10 can be a patient or a clinician using the web service 102 and the health management application 104 for different purposes. For example, during a healthcare consultation, a patient typically shares with a clinician a variety of patient data including blood glucose measurements, continuous glucose monitor data, insulin infused, food and beverages consumption, exercise, and other lifestyle information. This patient data can be recorded manually on a patient diary or other tools such as an Accu-Chek® 360 View Blood Glucose Analysis System form or electronically on a handheld diabetes manager, such as the handheld diabetes manager 12, or electronically on a personal computer (PC) 14 using diabetes analysis software, or electronically on a web-based diabetes analysis site or web service 102, or a combination of these means. The personal computer or computer processing device 14, as used herein, can be a desktop, laptop, tablet, smart phone or handheld processing device having any operating system, including operating systems by Microsoft Corporation (Windows and successors), by Apple Corporation (IOS and successors), by Linux or other operating systems, such as Android, webOS, etc. The personal computer 14 can include an electronic screen or display 20. The clinician will often obtain additional patient biomarker data such as measurements of HbA1C, cholesterol levels, triglycerides, blood pressure, and weight. The clinician can analyze the patient data using manual techniques, electronically using diabetes analysis software, or a web-based diabetes analysis site, such as the web service 102, the health management application 104 or a combination of these means. After analyzing the patient data along with the patient's adherence to the previously prescribed therapy, the clinician can decide whether to modify the therapy for the patient. In considering whether to modify the therapy, the clinician may need to balance the interests of the patient, the payer (not shown), and the clinician. Healthcare records systems such as Microsoft® HealthVault™ and Google™ Health can be used by the patient and clinician to exchange information via a communications network 40, such as the internet or web, communicating with the web service 102.

Accordingly, the user 10 (patient or clinician) may interact with a health management software (program or code) in the form of the health management application (HMA) 104 that may reside in the user's PC or other computer processing device 14 or in the web service 102, as shown in the exemplary illustration of FIG. 1, or both, or that may have submodules in both the PC and web service 102 that can be in communication (wired or wirelessly) via the internet or web or cellular network or other communications network 40. The user 10 may also connect the diabetes manager (or other portable device) 12 to the PC 14, wirelessly, by using a device reader or device dock or by USB connection for exchanging data, updating or installing software or other digital record management and transfer with either the same Health Management Application 104 or another local health management application (module or software) residing in the user's PC 14. The diabetes manager 12 can include an electronic screen or display 24. In other embodiments, the diabetes manager 12 can communicate directly with the web service 102 for data transfer and use the health management application 104 at the web service 102 or locally with a corresponding software module or health management application. The diabetes manger 12 can be a handheld device that can include a blood glucose (bG) meter and/or an insulin pump control device for a user 10 who is a patient. The diabetes manager 12 can also be a portable or handheld device used by a clinician to communicate with the patient, with the patient's diabetes manager, with clinical records of the patient's in the clinician's office and with the web service 102.

Figure 4:
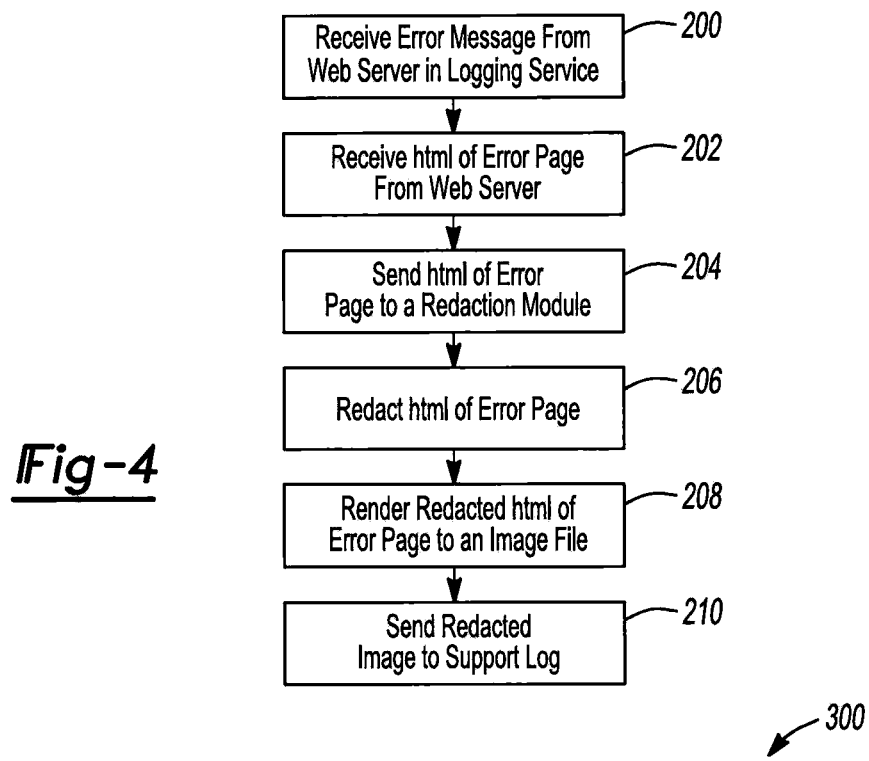
FIG. 4 is an exemplary flowchart of a method according to the present teachings.
Figure 5:
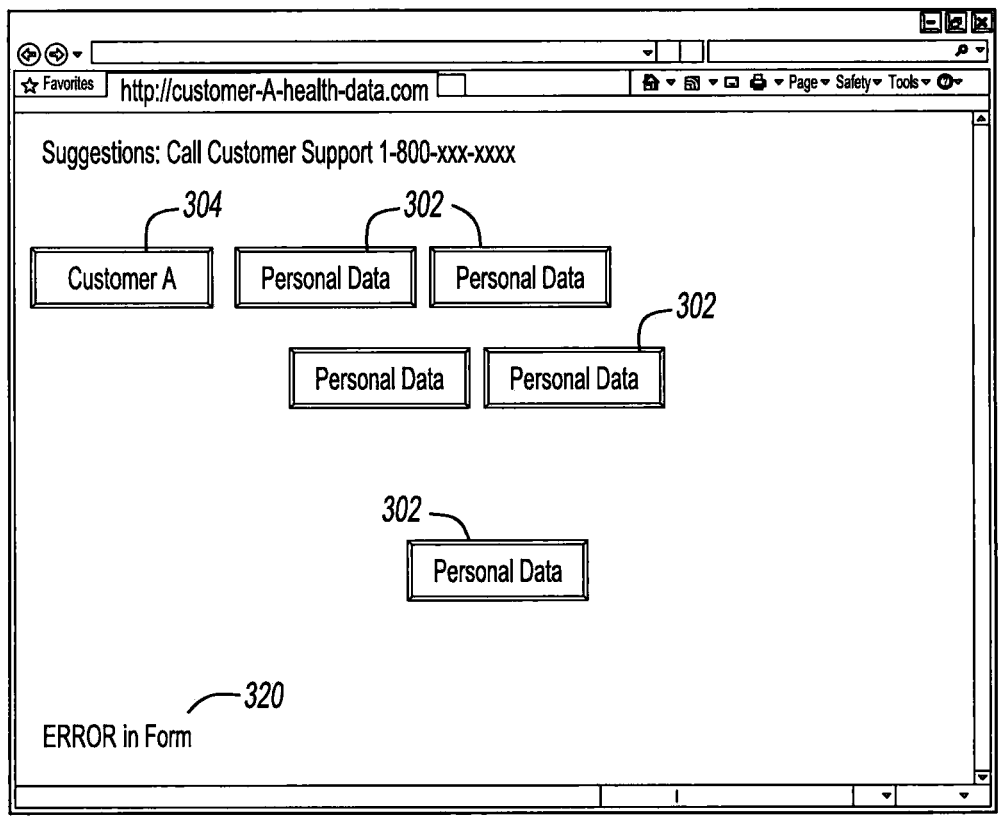
FIG. 5 is an illustration of an exemplary screen of a user session.

Referring to FIGS. 1-6, the user 10 can access the web service 102 and the health management application 104 using a personal user account and login or authentication credentials via the communications network 40. During an interactive session between the user 10 and the health management application 104, an error message 320 (see FIG. 5) may be displayed on the electronic screen 20 or 24 of the user 10. For example, the error message 320 may appear in the context of an electronic file or form that is displayed on a web page 300 of the user's web browsing application while accessing the web service 102 or the health management application 104, as shown in FIG. 5. The web page 300 may include various private data 302 associated with the user (Customer A at 304), such as, for example, bG values or other personal health values or medical history, social security number, health insurance information and identification or contract number, list of medications, various medical conditions, or other personal information, generally referenced herein as private information.

The error message 320 may relate to a failure to load a portion or the entire web page 300, formatting errors in a table or text or image associated with an electronic form of the health management application 104 displayed in the web page 300 or errors in tools or functions or other options associated with the web page 300 in the context of the health management application 104.

Figure 2:
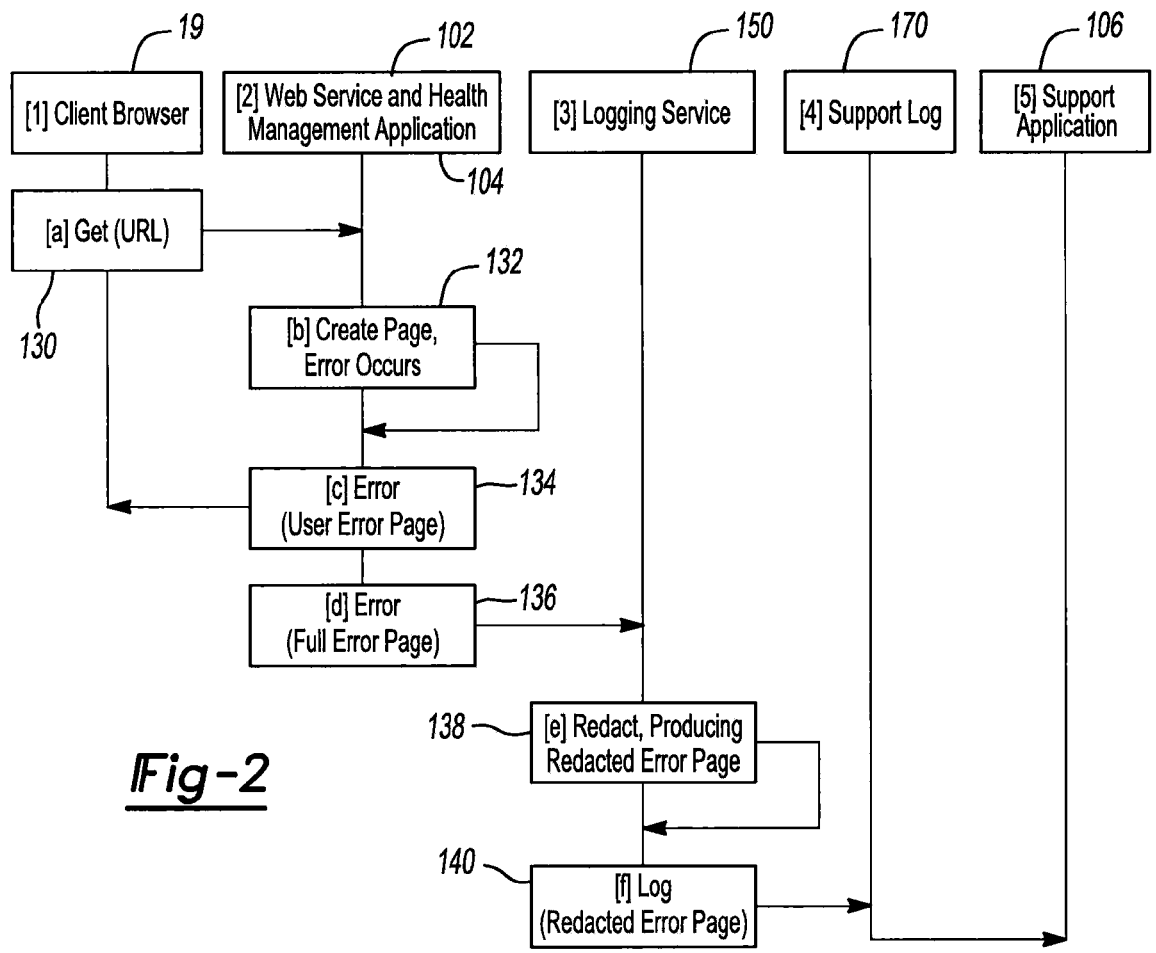
FIG. 2 is an exemplary sequence diagram of a method according to the present teachings.

Referring to the system diagram of FIG. 1 and the sequence diagram of FIG. 2, when the user 10 attempts to access the web service 102 and/or the health management application 104 using a web browser from the user's processing device 14 or 12 (such as a client browser 19 in FIG. 2) with a "get url" request at block 130, an error may occur during the creation of the corresponding web page (block 132) for the user 10. The web service 102 can send a web page with an error message (block 134) to be displayed in the electronic screen 20 or 24 of the user 10, such as the page shown in FIG. 5, and additionally send the web page with the error message in the form of an electronic file (block 136) to a logging service 150. From the logging service 150 the electronic file of the web page with the error can be transferred for redaction to a sanitization module 160 (FIG. 1). The sanitization module 160 can create a redacted error page (block 138), which can be logged (block 140) and stored in a support log 170 for access by a support person 52 at a later time.

As used above, a web browser is a software application or program designed to enable users to view, retrieve or generally access web pages, documents, images, video or other resources from the worldwide web, the internet or from web servers in private networks. Common web browsers include Internet Explorer, Safari, Firefox, Google Chrome, Opera and others. The web browser retrieves information identified by a "url", or Uniform Resource Information. The present teachings can also be extended to other applications.

More specifically, and referring to FIG. 3, the sanitization module 160 can include a redaction module 162 and an image rendering or image converting module 164. The electronic file of the web page with the error message can be received by the logging application 151 from the web service 102 in html (HyperText Markup Language) or other hypertext language or any other language that can be read by a web browser and converted to visible or audible content in a web page. In other embodiments, the electronic file can be associated with a particular web-implemented application, such as the health management application 104, and can be in any other language associated with the application, including languages used in mobile devices, such as smartphones and tablets, such as Objective-C, C, C++, JavaScript, Adobe Flash Builder, etc.

Figure 6:
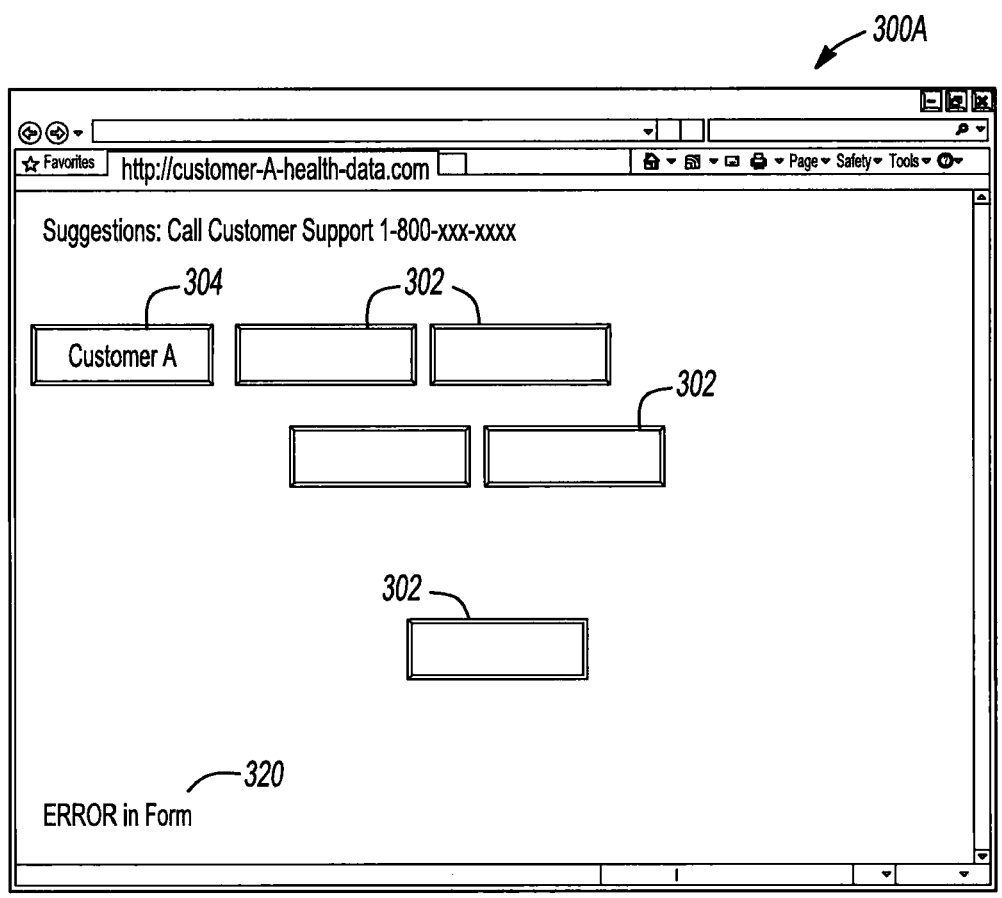
FIG. 6 is an illustration of a redacted screen corresponding to FIG. 5 according to the present teachings.

With continued reference to FIG. 3, the redaction module 162 can identify and redact private information according to instructions and rules programmed in the redaction module 162. For example, in one embodiment, fields 302 in a form or web page 300 (shown in FIG. 5) created by the health management application 104 and corresponding to private or otherwise protected information can be pre-tagged in the software of the health management application 104. The redaction module 162 is programmed to search for these pre-tagged fields and null or block their content or values to create a redacted electronic file. The redacted electronic file can be optionally processed in the image rendering module 164 to create an image of the redacted web page in image format, such as jpg, png, tiff or other image format, using a printer driver or other conversion software, as discussed below. Alternatively, areas known to contain private data can be pre-tagged in a profile of a health management form and these entire areas can be obscured by overlaying opaque geometric blocks or other image objects that obscure the underlying information. The redacted web page, either in electronic file form, such as html, or in image form can be delivered to the logging service 150 and/or to the support log 170. A support person 52 at the customer support service 50 can retrieve the redacted error page directly as an image from the support log 170. Additionally or alternatively, the redacted error page can be retrieved as a redacted html file that can be displayed on the electronic screen 56 of the processing device 54 of the support person 52 using a web browser of the support person 52. The support person 52 can communicate with the support application via communications network 40a, as shown in FIG. 1. A web page 300 with an error and private information is illustrated in FIG. 5 and a corresponding redacted page 300A is illustrated in FIG. 6, as discussed below.

An exemplary method for sanitizing a screen view or web page of the user 10 is summarized briefly in the flowchart of FIG. 4. An error message or other notification that an error occurred while processing a request by a user 10 of the web service 102 is received in the logging service at block 200. An electronic file of the web page with the error (300 in FIG. 5) is also sent to and received by the logging service 150 in html or other form (block 202). The electronic file is sent to the redaction module 162 at block 204 and is processed at the redaction module 162 to redact private information at block 206 to create a redacted electronic file. The redacted electronic file can be rendered or converted to an image file (block 208) in the image rendering module 164 to an image file. The image file with all the private data removed can be sent to and stored in a support log 170 (block 210). The rendering module 164 can include, for example, a printer driver module or other format converting module that can generate an image independent of the format of the original web page. The rendered redacted image can be retrieved by a support person 52 at a later time in response to a request for help from the user 10 or for a routine, scheduled or other error analysis, for update or upgrade of the web service 102 and health management application 104 or for other software or programming housekeeping or evaluation tasks.

As discussed above, the web page with the error message 300 can be retrieved and redacted in html form. The redacted page 300A can also be saved in html form to be viewed as a web page in the support person's browser or as an image file (jpg, png, tiff, etc.) to be viewed as an image in electronic screen 56 of the support person's processing device 54. FIG. 5 illustrates an exemplary web page 300 with an error message represented at 320 and including values in personal or private data fields 302 of a user 10, who is identified as customer A at 304. FIG. 6 is an exemplary corresponding redacted web page 300A, in which the values of the private data have been removed or otherwise blocked from fields 302.

It is appreciated that when an error message 320 is received by the web service 102, a history of requests to the web service 102 from the user's browser during the user's session associated with and prior to the error message 320 can also be sent to the logging service 150 for sanitization. Therefore, an entire history of the user's session can be archived in redacted electronic files (redacted html or image files) in the support log module 170.

Summarizing, according to the preset teachings, the user's screen view (such as a web page) associated with an error message or a sequence of screen views (a user's session) can be retrieved in real time, i.e., as the user 10 sees these views on the electronic display 20 (or 24). The corresponding electronic files of these screen views can be redacted by the sanitization module 160 and saved in the support log 170 for access at any time by a support person 52 of the customer support service 50. The support person 52 does not need to access the user's account and will not see any private information of the user 10, because such private information is already redacted. Any privacy regulations, such as HIPAA or other governmental regulations, are automatically respected. Additional mitigation efforts to ensure regulatory compliance regarding private information can be reduced or avoided.

When the user 10 contacts the customer support service 50 by telephone, cellular or network communication, the support person 52 can simply access the redacted web page 300A or an entire history of preceding redacted pages, without requesting access or having any access to the user's account and the user's protected private information.

As used herein, the phrase at least one of A, B, and C should be construed to mean a logical (A or B or C), using a non-exclusive logical or. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer-readable medium. The computer programs may also include stored data. Non-limiting examples of the non-transitory tangible computer readable medium are nonvolatile memory, magnetic storage, and optical storage.

The broad teachings of the disclosure can be implemented in a variety of forms. Therefore, while this disclosure includes particular examples, the scope of the disclosure should not be so limited since other modifications will become apparent to the skilled practitioner upon a study of the drawings, the specification, and the following claims.

What is claimed is:

1. A method for capturing a user's view of an electronic screen having an error message in a health management application without showing private information of the user, the method comprising:
    receiving the error message from a web service responding to a request for a web page by the user;
    receiving an electronic file of the web page, where content of the electronic file is defined in accordance with a markup language and the markup language has predefined presentation semantics;
    identifying fields in the electronic file that are pre-tagged as private information;
    redacting values of the identified fields in the electronic file to create a redacted electronic file, where content of the redacted electronic file is defined in accordance with the markup language having predefined presentation semantics; and
    storing the error message, along with the redacted electronic file, in a data store.

2. The method of claim 1, wherein redacting values includes identifying areas pre-tagged as private information in the electronic file and redacting the pre-tagged areas.

3. The method of claim 1, further comprising converting the redacted electronic file to an image file.

4. The method of claim 1, further comprising retrieving the redacted electronic file from the data store by a support person.

5. The method of claim 1, wherein the health management application is a diabetes management application.

6. The method of claim 1, further comprising:
   retrieving a history session of the user associated with and prior to the error message;
   redacting from each electronic file in the history session the private information of the user to create corresponding redacted electronic files of the history session; and
   storing the redacted electronic files of the history session in the data store.

7. The method of claim 1, wherein the electronic file and the redacted electronic file are in hypertext markup language.

8. A method for capturing a user's view of an electronic screen having an error message in a health management application without showing private information of the user, the method comprising:
   receiving the error message from a web service responding to a request for a web page by the user;
   receiving an electronic file of the web page with the error message;
   identifying fields pre-tagged as private information in the electronic file and redacting values associated with the pre-tagged fields to create a redacted electronic file;
   converting the redacted electronic file to an image file; and
   storing the image file in a support log module.

9. The method of claim 8, further comprising retrieving the redacted electronic file from the support log module by a support person.

10. The method of claim 8, wherein the health management application is a diabetes management application.

11. The method of claim 8, wherein the electronic file and the redacted electronic file are in hypertext markup language.

12. The method of claim 8, further comprising:
   retrieving a history session of the user associated with and prior to the error message;
   redacting from each electronic file in the history session the private information of the user to create corresponding redacted electronic files of the history session; and
   storing the redacted electronic files of the history session to the support log module.

13. A system for capturing a user's view of an electronic screen having an error message associated with a health management application without showing private information of the user, the system comprising:
   a computer processor;
   a logging service programmed to receive an electronic file with the error message from a user's electronic screen and transfer the electronic file for sanitization;
   a sanitization module programmed to receive the electronic file with the error message, redact private information of the user and create a redacted electronic file;
   a support log for receiving and storing the redacted electronic file; and
   a support application communicating with the support log and programmed to retrieve the redacted electronic file for delivery to a support person's processing device,
   wherein the logging service, the sanitization module, and the support application are all implemented by computer readable instructions executed by the computer processor.

14. The system of claim 13, wherein the sanitization module includes a redaction module programmed to create the redacted electronic file by identifying fields pre-tagged as private information in the electronic file and redacting values associated with the pre-tagged fields.

15. The system of claim 14, wherein the logging service is programmed to retrieve a history session of the user associated with and prior to the error message and transfer each electronic file to the redaction module.

16. The system of claim 15, wherein the redaction module is programmed to redact from each electronic file of the history session the private information of the user to create corresponding redacted electronic files of the history session.

17. The system of claim 13, wherein the sanitization module includes an image rendering module programmed to convert the redacted electronic file to an image file.

18. The system of claim 13, further comprising a web service communicating with a browser of the user in association with a health management application.

19. The system of claim 13, wherein the electronic file and the redacted electronic file are in hypertext markup language.

* * * * *